(12) United States Patent
Nunome

(10) Patent No.: US 7,520,859 B2
(45) Date of Patent: Apr. 21, 2009

(54) BLOOD PRESSURE MEASURING APPARATUS

(75) Inventor: Tomohiro Nunome, Komaki (JP)

(73) Assignee: Fukuda Denshi Co., Ltd., Tokyo (JP)

( * ) Notice: Subject to any disclaimer, the term of this patent is extended or adjusted under 35 U.S.C. 154(b) by 5 days.

(21) Appl. No.: 11/374,263

(22) Filed: Mar. 13, 2006

(65) Prior Publication Data

US 2006/0224068 A1 Oct. 5, 2006

(30) Foreign Application Priority Data

Mar. 16, 2005 (JP) .............................. 2005-075512

(51) Int. Cl.
*A61B 5/00* (2006.01)
(52) U.S. Cl. ...................... 600/490; 600/494
(58) Field of Classification Search .......... 600/485–507
See application file for complete search history.

(56) References Cited

U.S. PATENT DOCUMENTS

| | | | | |
|---|---|---|---|---|
| 4,947,855 A | * | 8/1990 | Yokoe et al. | 600/485 |
| 5,099,853 A | * | 3/1992 | Uemura et al. | 600/492 |
| 5,135,003 A | * | 8/1992 | Souma | 600/493 |
| 5,385,149 A | * | 1/1995 | Chang et al. | 600/493 |
| 5,582,179 A | * | 12/1996 | Shimizu et al. | 600/500 |
| 5,961,467 A | * | 10/1999 | Shimazu et al. | 600/485 |
| 6,310,646 B1 | * | 10/2001 | Shi et al. | 348/194 |
| 2002/0188206 A1 | * | 12/2002 | Davis et al. | 600/485 |
| 2007/0049834 A1 | * | 3/2007 | Tao et al. | 600/494 |

FOREIGN PATENT DOCUMENTS

| JP | 59-95033 | | 5/1984 |
|---|---|---|---|
| JP | 05111468 A | * | 5/1993 |

OTHER PUBLICATIONS

Shimazu Hideaki "Blood Pressure" Mar. 15, 2001 p. 112-116.

* cited by examiner

*Primary Examiner*—Robert L Nasser
(74) *Attorney, Agent, or Firm*—Merchant & Gould P.C.

(57) ABSTRACT

A blood pressure measuring apparatus to measure blood pressure based on a change in a pressure by a cuff mounted to a subject comprises: cuff pressure controlling means for deflating the cuff after avascularization by the cuff at a body part around which the cuff is placed; detecting means for detecting the change in a pressure by the cuff and outputting the detection as an electrical signal; extracting means for extracting a pulse wave signal from the electrical signal; and calculating means for calculating a systolic blood pressure value and a diastolic blood pressure value based on a relation between a change rate of an index value which is calculated by multiplying a maximum amplitude of each pulse of the pulse wave signal by the cuff pressure corresponding to the maximum amplitude and a predetermined value. The blood pressure measuring apparatus achieves a high-speed measurement while suppressing the reduction of accuracy.

6 Claims, 5 Drawing Sheets

BLOOD PRESSURE MEASURING APPARATUS

CLAIM OF PRIORITY

This application claims priority from Japanese Patent Application No. 2005-075512, filed on Mar. 16, 2005, which is hereby incorporated by reference herein.

FIELD OF THE INVENTION

The present invention relates to a blood pressure measuring apparatus, in particular, to an automated blood pressure measuring apparatus using a cuff.

BACKGROUND OF THE INVENTION

Conventionally, an oscillometric technique is known to measure blood pressure non-invasively. In the oscillometric technique, a cuff is fitted around a limb such as a brachium of a subject to detect pulse waves at the body part by the cuff and a blood pressure is measured based on the fact that the volume of the blood vessel under the cuff changes most at the point when the pressure applied by the cuff to the blood vessel becomes equal to a mean blood pressure thereof.

Specifically, the cuff is inflated to press the body part for avascularization, and as the cuff is being deflated, the cuff pressure is detected until the pressure goes below a diastolic blood pressure thereof to obtain pressure signals to which pulse wave signals are superimposed. The pulse wave signals are separated from the pressure signals by a filter to determine that the cuff pressure value at the point at which the maximum amplitude through the entire period of the separated pulse wave signals (i.e. maximum peak-to-peak value; hereinafter, "an amplitude" is used as a peak-to-peak value) was observed equals to a mean blood pressure thereof. The systolic blood pressure and the diastolic blood pressure are generally determined to be the cuff pressure values at which an amplitude under a predetermined condition is detected respectively based on the maximum amplitude (for example, see Shimazu Hideaki, "Blood Pressure", Mar. 15, 2001, pp. 112-116).

The automated blood pressure measuring apparatus by the oscillometric technique are widely used since a blood pressure can be measured relatively easily, however, they require a certain time for measurement. This is mainly because a blood pressure value is determined based on the maximum amplitude of detected pulse wave signals in such conventional blood pressure measuring apparatus.

In order to shorten the time for measurement, a cuff deflation rate after avascularization needs to be increased; however, the increased cuff deflation rate makes it difficult to detect the maximum amplitude of pulse waves with high accuracy, which in turn results in increasing errors in blood pressure values.

The pulse wave signals are not detected when the cuff pressure on a body part goes below a diastolic blood pressure thereof. As far as the pulse rate does not change, the higher deflation rate allows only the fewer pulses of pulse wave signals to be detected. Moreover, because the higher deflation rate makes the time around which the cuff pressure equals to the mean blood pressure shorter, the timing of the largest amplitude of the pulse waves may be offset from the timing around which the cuff pressure equals to the mean blood pressure with high possibility.

Meanwhile due to the above factors the increased deflation rate makes it difficult to detect the maximum amplitude with high accuracy, there is a demand from subjects for quick release from the pressure by a cuff after avascularization because the pressure is not comfortable.

SUMMARY OF THE INVENTION

The present invention is accomplished in the view of the above problems in the prior art, and it is an object of the present invention to provide a blood pressure measuring apparatus which measures blood pressure quickly while suppressing the reduction of accuracy.

To achieve the above object, a blood pressure measuring apparatus according to the present invention measures blood pressure based on a change in a pressure by a cuff mounted to a subject, and comprises: cuff pressure controlling means for deflating a cuff after avascularization by the cuff at a body part around which the cuff is placed; detecting means for detecting the change in a pressure by the cuff and outputting the detection as an electrical signal; extracting means for extracting a pulse wave signal from the electrical signal; and calculating means for calculating a systolic blood pressure value and a diastolic blood pressure value based on a relation between a change rate of an index value which is calculated by multiplying a maximum amplitude of each pulse of the pulse wave signals by a cuff pressure corresponding to the maximum amplitude and a predetermined value.

The above object is also achieved by a medical apparatus which comprises a blood pressure measuring apparatus according to the present invention and has means for using the calculated systolic blood pressure value and the diastolic blood pressure value.

This configuration, according to the present invention, makes it possible to measure blood pressure at high speed while suppressing the reduction of accuracy, because it determines blood pressure value independently of a maximum amplitude value.

Other objects and advantages besides those discussed above shall be apparent to those skilled in the art from the description of a preferred embodiment of the invention which follows. In the description, reference is made to accompanying drawings, which form a part thereof, and which illustrate an example of the various embodiments of the invention. Such example, however, is not exhaustive of the various embodiments of the invention, and therefore reference is made to the claims which follow the description for determining the scope of the invention.

BRIEF DESCRIPTION OF THE DRAWINGS

The accompanying drawings, which are incorporated in and constitute a part of the specification, illustrate embodiments of the invention and, together with the description, serve to explain the principles of the invention.

DETAILED DESCRIPTION OF THE PREFERRED EMBODIMENTS

<Configuration of Blood Pressure Measuring Apparatus>

Figure 1:
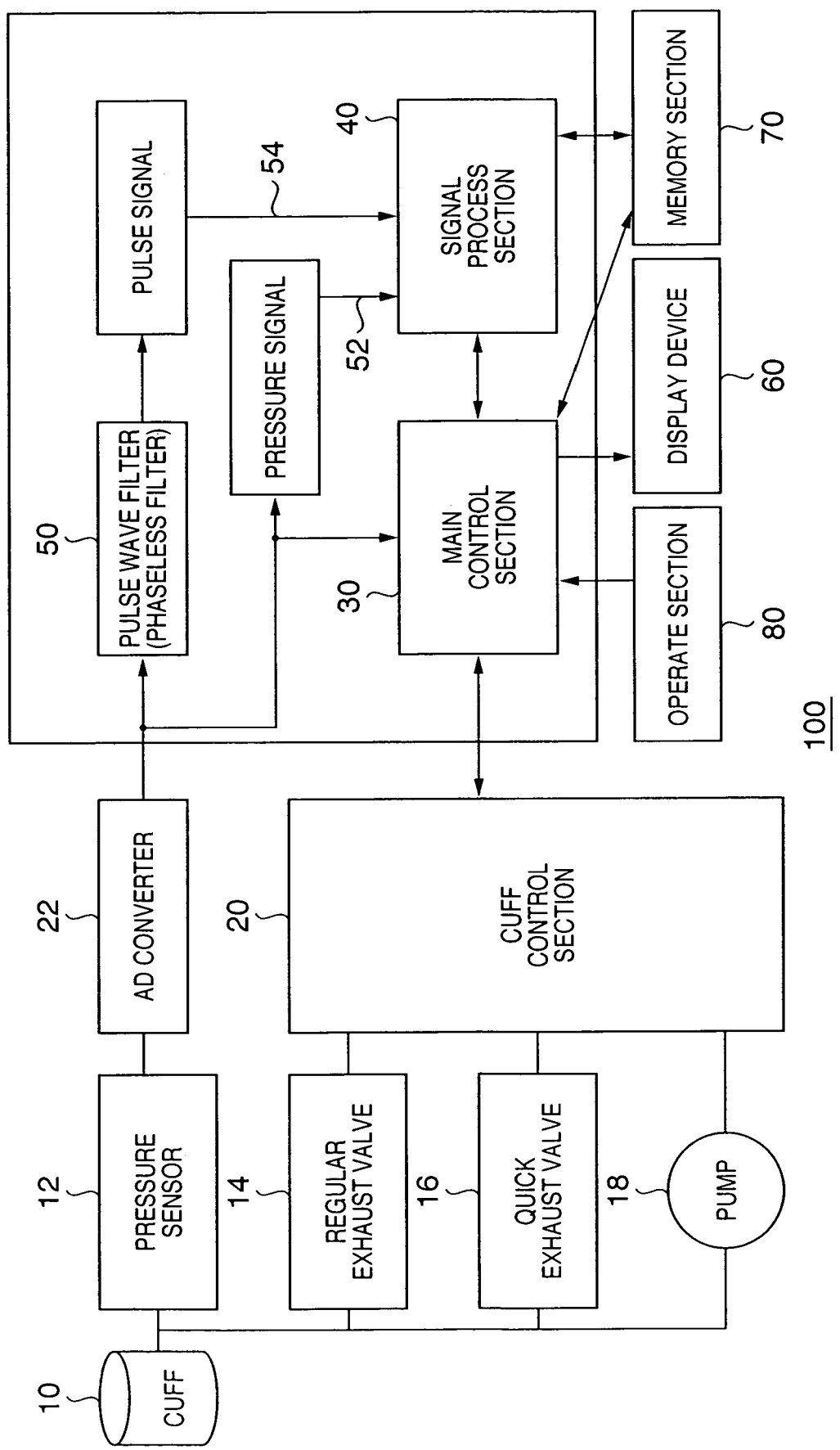
FIG. 1 is a block diagram to illustrate an example of a configuration of a blood pressure measuring apparatus according to an embodiment of the present invention.

FIG. 1 is a block diagram to illustrate an example of a configuration of a blood pressure measuring apparatus 100 according to an embodiment of the present invention. The blood pressure measuring apparatus 100 includes a cuff 10 having an air bag (not shown in it), and the cuff 10 is fitted around a body part of a subject to press the body part by inflating the air bag by a pump 18 which is connected thereto. The cuff 10 may be fitted around any body part for avascularization, usually being fitted around one of the limbs. The air bag is connected a regular exhaust valve 14 and a quick exhaust valve 16 for exhaustion, and the regular exhaust valve 14 is opened during pulse waves being detected after avascularization until a blood pressure is determined, and the quick exhaust valve 16 is also opened after the determination of the blood pressure, under the controls of a cuff control section 20 respectively. The cuff control section 20 controls the pump 18, the regular exhaust valve 14, and the quick exhaust valve 16 according to the control of a main control section 30 which will be described below, and also controls a cuff pressure during measurement.

The regular exhaust valve 14 exhausts less air in a unit time than the quick exhaust valve 16, which is on the order of 5 mmHg/second in a conventional blood pressure measuring apparatus. On the contrary, in a blood pressure measuring apparatus of this embodiment, the regular exhaust valve 14 exhausts air of 10 mmHg/second which still allows measurements of blood pressure with good accuracy.

The air bag of the cuff 10 is also connected to a pressure sensor 12 other than the regular exhaust valve 14, the quick exhaust valve 16, and the pump 18. The pressure sensor 12 may be a pressure-electricity conversion type of sensor using for example a piezo element and the like, and converts the pressure inside of the cuff (air bag) into an electrical signal for output. The electrical signals (pressure signals) are sampled at a predetermined frequency by an AD converter 22 and stored as digital data. The digital data of pressure signals 52 are supplied to a signal process section 40 and a pulse wave filter 50.

The pulse wave filter 50 extracts pulse wave signals which are included in the pressure signals. The pulse wave filter 50 may be realized by a band pass filter which transmits general pulse frequencies. When the pulse wave filter 50 is an analogue filter, the analogue filter may be arranged so that the output from the pressure sensor 12 is directly input into the pulse wave filter 50 and another AD converter 22 is placed in a subsequent stage of the pulse wave filter 50.

Figure 3:
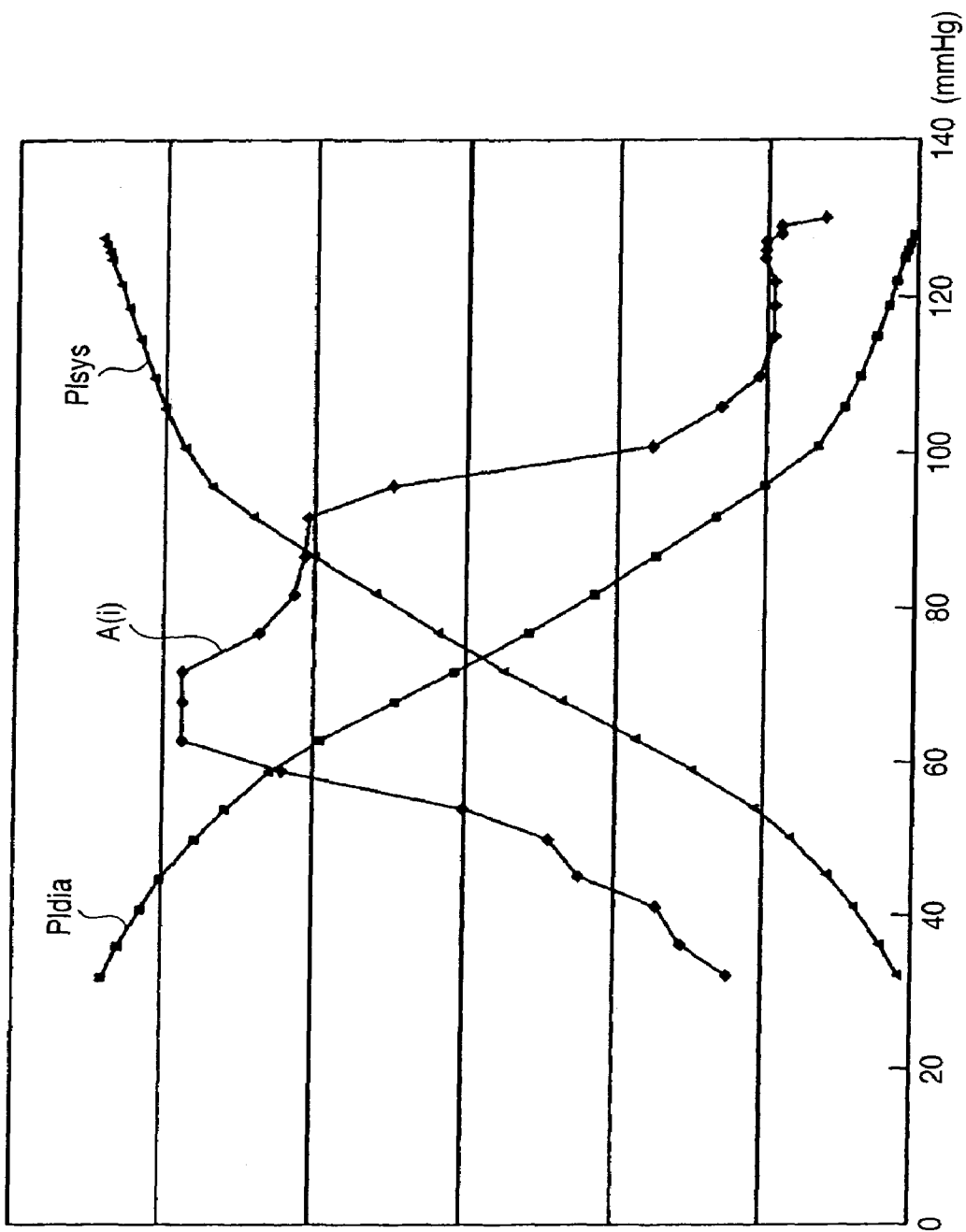
FIG. 3 is a diagram to illustrate an actual example of values calculated by a blood pressure measuring apparatus according to an embodiment.

In this embodiment, the pulse wave filter 50 is a phaseless filter configured with a digital filter to suppress waveform distortion by phase characteristics of a filter. The phaseless filter compensates the phase characteristics of a band pass filter by processing an input signal with a band pass filter and again processing the input signal with a band pass filter having the same characteristics with the previous band pass filter after reversing the time axis of the input signal. The digital data of the input signals allow the time-reversed signals to be produced easily by sorting the signal samples. The phaseless filter is well known in the art as shown in FIG. 3 of JP Patent Publication (Kokai) No. 59-95033, and thus, will not be discussed or illustrated in detail herein.

Figure 2:
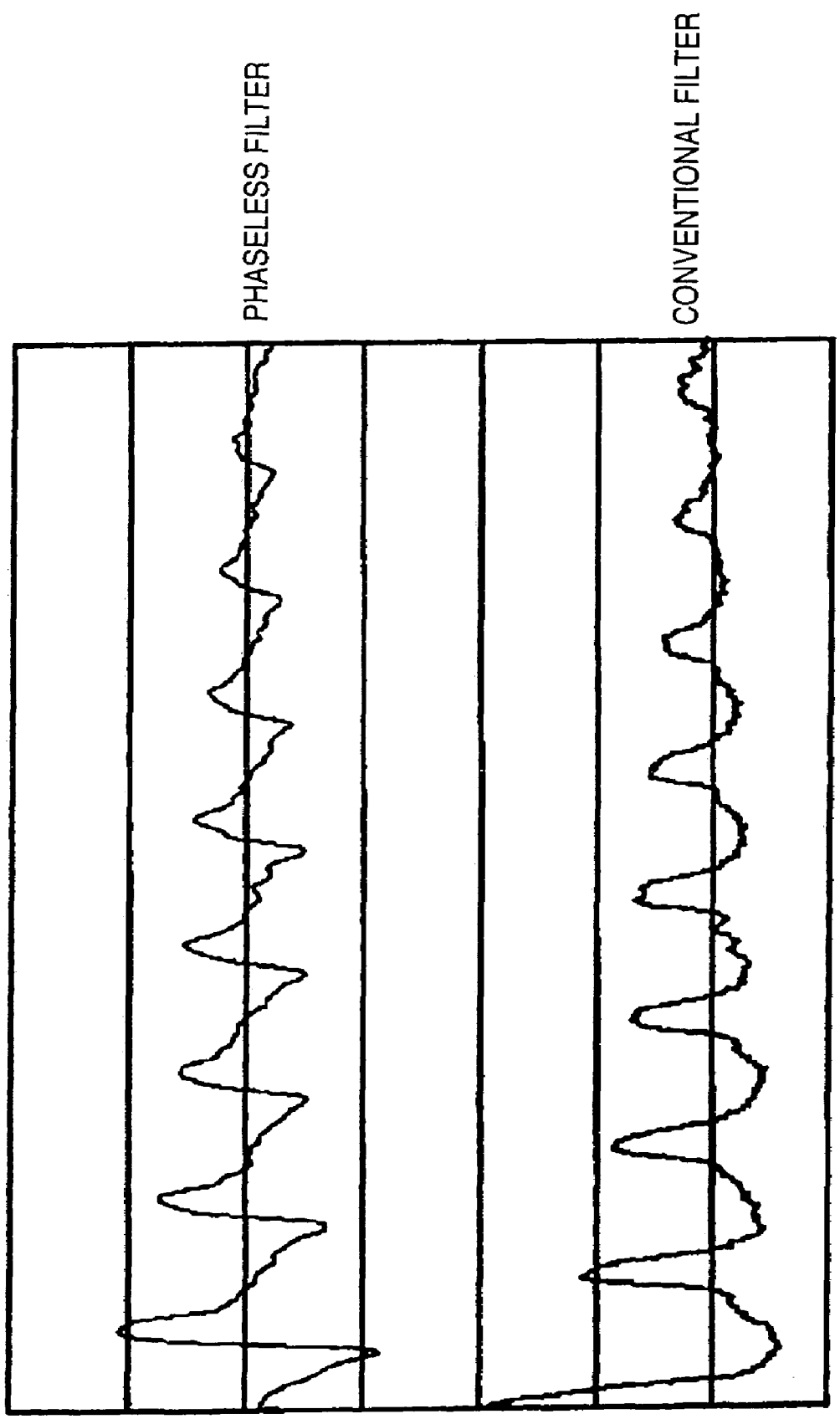
FIG. 2 is a diagram to illustrate an example of pulse signals extracted by processing the same pressure signals by a phaseless filter and a conventional analogue filter.

Extracting pulse waves using a phaseless filter without rounding the waveforms improves the detection accuracy in pulse wave amplitudes for each pulse, which in turn contributes to an improvement in the measurement accuracy of blood pressure values. FIG. 2 illustrates pulse wave signal waveforms resulting from the same pressure signal processed and extracted by a phaseless filter and a conventional analogue filter respectively. This shows that the waveform by an analogue filter is distorted although both filters have the same pass band.

Turning back to FIG. 1, the pulse signal 54 extracted by the pulse wave filter 50 and the pressure signal 52 output by the AD converter 22 are input into the signal process section 40. The signal process section 40 executes a blood pressure determining process with the pressure signal 52 and the pulse signal 54, which will be explained below, to determine a diastolic blood pressure value and a systolic blood pressure value. The determined blood pressure values are transmitted to the main control section 30.

The main control section 30 controls the entire operation of the blood pressure measuring apparatus 100 to perform an automated blood pressure measurement. Though, in FIG. 1, the main control section 30, the signal process section 40 and the pulse wave filter 50 are illustrated as individual elements, practically a microprocessor (CPU) may execute control software to perform these functions of these sections to implement them so-called in software.

The display device 60 includes a dot matrix display such as LCD and an LED lump and the like, and, according to the main control section 30, displays an operating state of the blood pressure measuring apparatus 100, a result of measurement, a guidance, and the like by using a graphical user interface (GUI) for example. Instead of or in addition to the display device 60, other output devices such as speakers and printers may be included.

The memory section 70 is a memory device to store information which is necessary for the blood pressure measuring apparatus 100 to operate, information which is input for measurements (e.g. information of subjects), measurement data, and the like, and includes a semiconductor memory, a magnetic recording apparatus such as a hard disc drive, and the like. When the main control section 30, the signal process section 40 and the pulse wave filter 50 and the like are implemented in software, the control program which is executed by a CPU is stored in the memory section 70. The memory section 70 is also used as a work area for the CPU.

The memory section 70 may include a combination of a plurality of memory devices such as a combination of an integrated memory and a memory card reader.

The operate section 80 includes keys, buttons, a touch panel which is mounted to the display device 60, and is used to allow a user to give a command to the blood pressure measuring apparatus 100. The operation of the operate section 80 is monitored by the main control section 30.

<Method to Determine Blood Pressure>

Now, a method to determine blood pressure with a blood pressure measuring apparatus of this embodiment will be explained. As described above, a conventional oscillometric blood pressure measuring apparatus determines a blood pressure based on the maximum amplitude of the extracted pulse waves through a whole period (all the pulses); while in the apparatus, an increased cuff deflation rate lowers the measurement accuracy of the maximum amplitude, which means it is difficult to increase a cuff deflation rate with maintaining measurement accuracy.

To the contrary, the blood pressure measuring apparatus of this embodiment determines a blood pressure independently of the maximum amplitude of pulse waves so that an increased cuff deflation rate is achieved with maintaining measurement accuracy. A method to determine blood pressure of this embodiment will be explained below.

In this embodiment, a systolic blood pressure and a diastolic blood pressure are determined by using an index (PI value) expressed in Formula (1) as follows:

To detect a diastolic blood pressure $$PIdia(i)=PIdia(i-1)+A(i)\times\{P(i-1)-P(i)\}$$

To detect a systolic blood pressure $$PIsys(i)=PIsys(i+1)+A(i)\times\{P(i)-P(i+1)\} \quad \text{Formula (1)}$$

where i is a number for each measurement data which is assigned serially beginning with 1, 2, 3, and so on to the cuff pressures in order from the highest to the lowest. Generally, i at the detected diastolic blood pressure is equal to the number for the measured pulses.

$A(i)$ is the maximum amplitude of the ith pulse, and $P(i)$ is the cuff pressure (mmHg) at the point where $A(i)$ is observed. Both $PIdia(0)$ and $PIsys(imax)$ are zero, where imax is the maximum value of i.

As seen clearly from Formula (1), PI is an integrated value by multiplying the maximum amplitude of each pulse by a cuff pressure which changed during the measurement of the maximum amplitude. PIdia is calculated with the value of i being increased from 1, and PIsys is calculated with the value of i being decreased from imax.

The $P(i)$s at which the PI values meet the condition of Formula (2) or (2') are determined to be a systolic blood pressure and a diastolic blood pressure.

Diastolic Blood Pressure $$PIdia(i-1)/PIdia(i)>\text{constant}$$

or $$PIdia(i-1)/PIdia(i)>\{P(i)+\alpha\}/\{P(i-1)+\alpha\}$$

Systolic Blood Pressure $$PIsys(i+1)/PIsys(i)>\text{constant}$$

or $$PIsys(i+1)/PIsys(i)>P(i+1)/P(i) \quad \text{Formula (2)}$$

Diastolic Blood Pressure $$PIdia(i-1)>\text{constant}\times PIdia(i)$$

or $$PIdia(i-1)\times\{P(i-1)+\alpha\}>\{P(i)+\alpha\}\times PIdia(i)$$

Systolic Blood Pressure $$PIsys(i+1)>\text{constant}\times PIsys(i)$$

or $$PIsys(i+1)\times P(i)>P(i+1)\times PIsys(i) \quad \text{Formula (2')}$$

Formula (2') is another expression of Formula (2) without division. Formula (2') is preferable to reduce errors and processing loads in the calculation process by computer.

A diastolic blood pressure and a systolic blood pressure are determined base on a relation between a change rate of PI value and a predetermined value in the way described above. Although more consideration should be given to the predetermined value (the right member of the inequalities) which is to be compared to a change rate of PI value, i.e. whether the predetermined value should be a constant or not, the lower Formulas where the predetermined value is set as a function of a cuff pressure presently provide better results with higher accuracy than the upper Formulas. In this regard, α is a constant. As for a diastolic blood pressure, the addition of a provides better results with fewer errors.

FIG. 3 illustrates the amplitudes $A(i)$, $PIdia(i)$, and $PIsys(i)$ which are calculated from actual measurements of pulse signals and pressure signals. The $PIdia(i)$ and $PIsys(i)$ schematically shows the ways to integrate cuff pressures in order from the highest to the lowest and in order from the lowest to the highest respectively.

Practically, the values of i increase from the right side to the left side of FIG. 3 for $PIdia(i)$ (the cuff pressures are integrated in order from the highest to the lowest), and from the left side to the right side of FIG. 3 for $PIsys(i)$ (the cuff pressures are integrated in order from the lowest to the highest).

In the conventional method to determine blood pressure, the pressure where the measured pulse amplitude constitutes a certain percentage of the maximum amplitude of measured pulses (such as 60%) is determined to be a systolic blood pressure or a diastolic blood pressure. Thus, errors in the measured pulse amplitudes may lead wrong measurements. This means an increased cuff deflation rate increase the errors in the measured pulse amplitudes, which in turn increases errors in the measurements. To the contrary, in the method of this embodiment, a blood pressure value is determined based on a change of an integrated value of a pulse amplitude to a cuff pressure without using the maximum amplitude of measured pulses. This enables the deflation rate of a cuff to be increased without loss of accuracy compared to the conventional method since the error in each pulse amplitude does not greatly influence the determination result.

<Operation of Blood Pressure Measuring Apparatus>

Now, the process to measure blood pressure with the above described method will be explained using the flow charts in FIG. 4 and FIG. 5.

Figure 4:
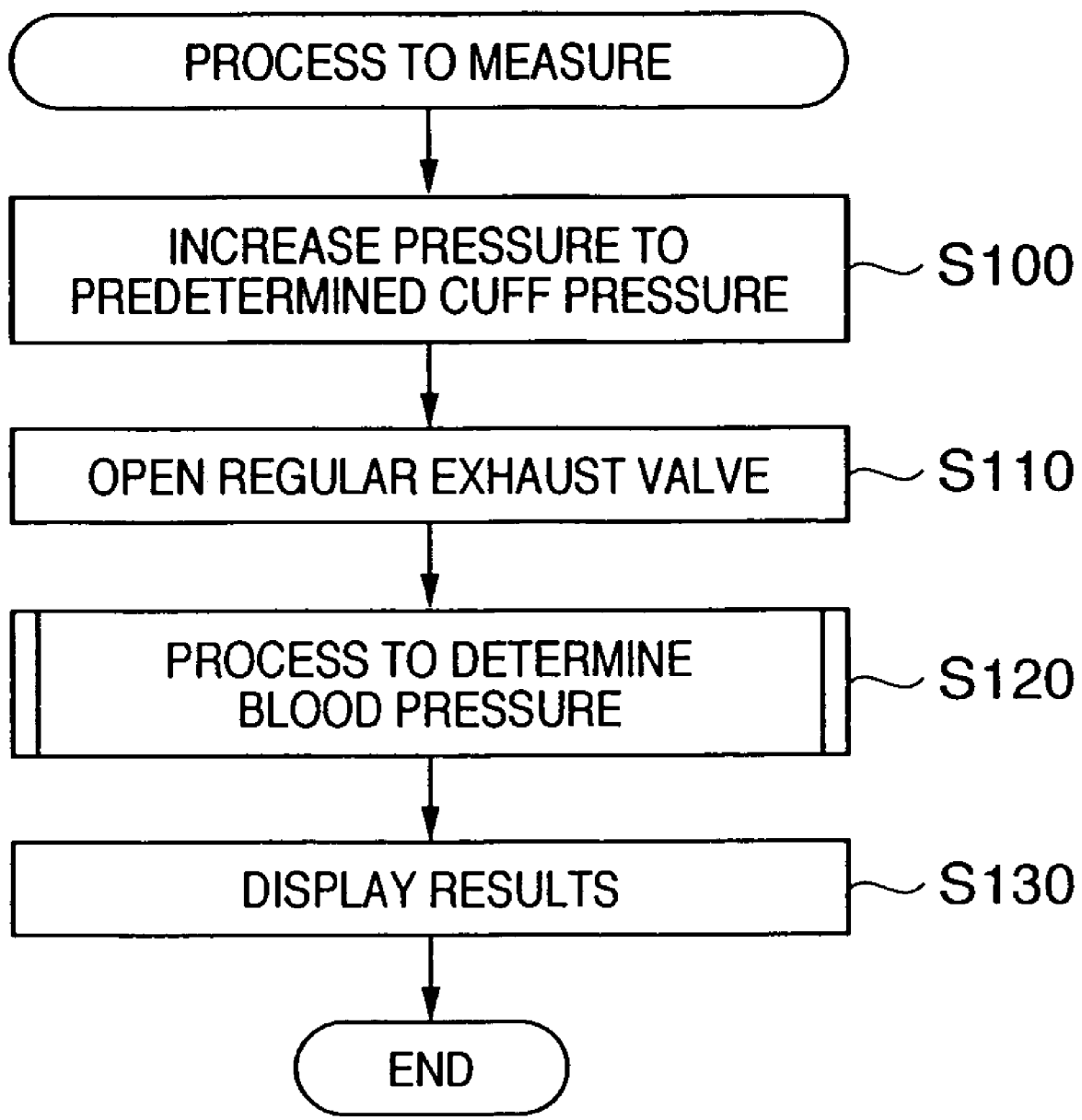
FIG. 4 is a flow chart to schematically illustrate an entire process flow of a blood pressure measuring apparatus according to an embodiment.
Figure 5:
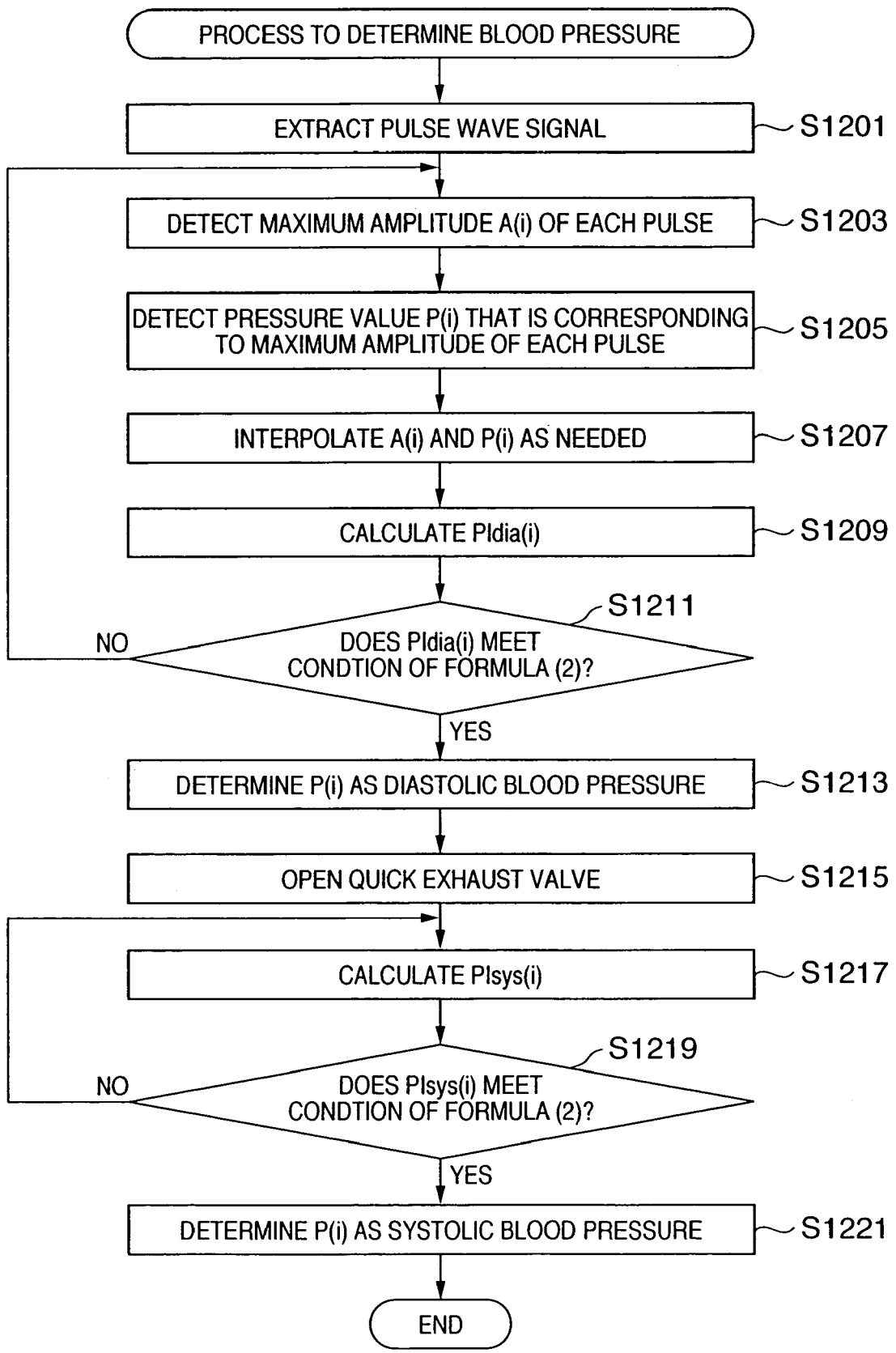
FIG. 5 is a flow chart to illustrate a process to determine blood pressure of FIG. 4 in detail.

FIG. 4 is a flow chart to illustrate an entire operation of a blood pressure measuring apparatus according to the embodiment. Pushing for example a start button of the operate section 80 as a command to start an operation for measurement causes the main control section 30 to control the cuff control section 20 to supply air to the air bag by the pump 18 so that the pressure of the cuff 10 is increased. The pressure of the cuff 10 is detected via the pressure sensor 12 and the AD converter 22, and when the detected pressure reaches a predetermined target pressure (a pressure for avascularization), the pump 18 is stopped (S100).

Next, the main control section 30 controls the cuff control section 20 to open a regular exhaust valve 14 to start the deflation of the air bag in the cuff 10 (S110). In the blood pressure measuring apparatus of the embodiment, the deflation is possible at a high rate of about 10-12 mmHg/second.

Upon the opening of the regular exhaust valve 14, the main control section 30 controls the pulse wave filter 50 and the signal process section 40 to operate to start the process to determine blood pressure (S120). The process to determine blood pressure will be explained in detail below using FIG. 5. When a blood pressure value is normally determined by the process to determine blood pressure, the result is transmitted from the signal process section 40 to the main control section 30 to be displayed at the display device 60 (S130). The measurement result may be output to other external devices such as a printer (not shown).

The process to determine blood pressure at step S120 of FIG. 4 will be explained in detail below using a flow chart of FIG. 5.

At S1201, the pulse wave filter 50 processes a pressure signal from the AD converter 22 to extract a pulse signal 54.

The signal process section 40 derives PIdia(i) in accordance with the above described Formula (1) using the pressure signal 52 from the AD converter 22 and the pulse signal 54 from the pulse wave filter 50 as follows.

First, at S1203, a maximum amplitude (p-p) of each pulse in the pulse signal 54 is detected and stored in the memory section 70 as A(i). Also, a pressure value P(i) corresponding to the A(i) is detected from the pressure signal 52 and stored in the memory section 70 in corresponding relation to the A(i). Alternatively, the signal process section 40 may first store the pressure signal 52 and the pulse signal 54 into the memory section 70, and next serially read out the signals to detect A(i) and P(i).

Next, the signal process section 40 interpolates P(i) and A(i) as needed due to, for example, the large difference between P(i) and P(i+1) (e.g. over 5 mmHg) (S1207). Specifically, a new value P(i+1) which is the middle value between P(i) and P(i+1) is inserted, and the original P(i+1) is set to be P(i+2). For the subsequent values, similarly the interpolation is performed. In addition, a new value which is the middle value between A(i) and A(i+1) is produced as a new A(i+1), which corresponds to the new P(i+1). The interpolated values are stored in the memory section 70 in the same way as the actually measured values.

In the interpolation, it is practically desirable to store a plurality of pulse signals 54 and pressure signals 52 for several pulses in the memory section 70, and sort the signals in accordance with the pressures in order from the highest to the lowest for interpolation process. In this regard, A(i)s and P(i)s are usually obtained in order from the highest to the lowest without otherwise sorting them. Also, the sorting may be done even when no interpolation is performed. In this case, the sorting may be done right before the deriving of PIdia(i).

The signal process section 40 calculates PIdia(i) using Formula (1) (S1209). The signal process section 40 reads out values which are necessary for the calculation from the memory section 70, and uses them. The calculated PIdia(i) is stored in the memory section 70, and at the same time, is determined if it satisfies the condition of Formula (2) or Formula (2') to determine a diastolic blood pressure (S1211).

When the calculated PIdia(i) satisfies the condition of Formula (2) or Formula (2') to determine a diastolic blood pressure, the step goes forward to S1213 to determine the P(i) as a diastolic blood pressure value. When the calculated PIdia(i) does not satisfy the condition, the step goes backward to S1203 to repeat the process described above.

After a diastolic blood pressure is determined at S1213, the signal process section 40 reports the diastolic blood pressure value (or only the fact that the diastolic blood pressure value is determined) to the main control section 30. In response to the report, the main control section 30 controls the cuff control section 20 to open the quick exhaust valve 16 (S1215). At this time, the main control section 30 may display the reported diastolic blood pressure value at display device 60.

While, the signal process section 40 subsequently implements a process to determine a systolic blood pressure value. In the process to determine a diastolic blood pressure value, A(i) and P(i) which are necessary to determine a systolic blood pressure are already calculated and stored in the memory section 70. Thus, the signal process section 40 reads out the A(i) and P(i) stored in the memory section 70 serially in accordance with the blood pressure values in order from the lowest (A(imax) and P(imax)), and calculates PIsys(i) using Formula (1) (S1217).

The calculated PIsys(i) is stored in the memory section 70, and at the same time, is determined if it satisfies the condition of Formula (2) or Formula (2') to determine a systolic blood pressure (S1219). When the calculated PIsys(i) satisfies the condition of Formula (2) or Formula (2') to determine a systolic blood pressure, the step goes forward to S1221 to determine the P(i) as a systolic blood pressure value. When the calculated PIsys(i) does not satisfy the condition, the step goes backward to S1217 to calculate next PIsys(i).

After a systolic blood pressure is determined at S1221, the signal process section 40 reports the systolic blood pressure value (or diastolic blood pressure value and systolic blood pressure value) to the main control section 30 to end the process to determine blood pressure.

In the event of any failure which is not explained herein in particular (for example, a cuff pressure is abnormal, no pulse waves is detected, or no blood pressure value is determined), error processing including a termination of reporting or measurement and a remeasurement is performed as in a conventional automated blood pressure measuring apparatus.

EXAMPLE

In a blood pressure measuring apparatus having a configuration of FIG. 1, a phaseless filter configured with a high-pass filter and a low-pass filter having the characteristics of Formula (3) below was used as the pulse wave filter 50. A blood pressure was actually measured using the lower formula of Formula (2') as a condition to determine a blood pressure, with a deflation rate of a cuff pressure by opening the regular exhaust valve 14 being 10 mmHg/second, a sampling period by the AD converter 22 being 4 ms. The constant a in the Formula to determine a diastolic blood pressure was 20.

HPF [Formula 3]

$$\text{Pulse}(i) = P\left(z^{-199} - \left(\frac{1}{200} \cdot \frac{1 - z^{-200}}{1 - z^{-1}}\right)^2\right)$$

LPF $$Pul(i) = \text{Pulse}(i)\left(\frac{1}{7} \cdot \frac{1 - z^{-7}}{1 - z^{-1}}\right)^3$$

About 1300 measurements were performed, and as a result the difference to the measurement value with a direct method is: mean error −3.68 mmHg and standard deviation 7.56 mmHg for systolic blood pressure; and mean error 3.28 mmHg and standard deviation 5.9 mmHg for diastolic blood pressure. American National Standards Institute/the Association for the Advancement of Medical Instrumentation SP-10 sets a standard which an automated blood pressure measuring apparatus should meet, and according to the standard, the mean error needs to be ±5 mmHg or less and the standard deviation needs to be 8 mmHg or less. The results showed that the blood pressure measuring apparatus having a configuration of FIG. 1 is capable to measure blood pressures in conformance with the standard.

The blood pressure measuring apparatus can be used as a single unit, as well as can be preferably incorporated and used in any other medical apparatus which requires blood pressure measurement, such as a monitoring apparatus, ABI measuring apparatus. Though in conventional blood pressure measuring apparatus the deflation rate is about 5 mmHg/second, the blood pressure measuring apparatus according to the embodiment achieves a measurement at a higher deflation rate of more than twice that of conventional blood pressure measuring apparatus, which makes the burden on a subject much lighter.

As many apparently widely different embodiments of the present invention can be made without departing from the spirit and scope thereof, it is to be understood that the invention is not limited to the specific embodiments thereof except as defined in the appended claims.

What is claimed is:

1. A blood pressure measuring apparatus to measure blood pressure based on a change in a pressure by a cuff mounted to a subject, comprising:
   cuff pressure controlling means for deflating the cuff after avascularization by the cuff at a body part around which the cuff is placed,
   detecting means for detecting the change in a pressure by the cuff and outputting the detection as an electrical signal,
   extracting means for extracting a pulse wave signal from the electrical signal, and
   calculating means for calculating a systolic blood pressure value and a diastolic blood pressure value based on a relation between (1) a change rate of an index value which is calculated in part by multiplying a maximum amplitude of each pulse of the pulse wave signal by a cuff pressure differential at the maximum amplitude and (2) a predetermined value.

2. The blood pressure measuring apparatus according to claim 1, wherein the calculating means calculates a systolic blood pressure value and a diastolic blood pressure value based on a relation between a change rate of an integrated value of the index value and the predetermined value.

3. The blood pressure measuring apparatus according to claim 1, wherein the predetermined value is a change rate of the cuff pressure corresponding to the maximum amplitude.

4. The blood pressure measuring apparatus according to claim 1, wherein the predetermined value is a predetermined fixed value.

5. The blood pressure measuring apparatus according to claim 1, wherein the extracting means is a phaseless filter.

6. A medical apparatus, comprising: a blood pressure measuring apparatus according to claim 1; and means for using the calculated systolic blood pressure value and the diastolic blood pressure value.

* * * * *

UNITED STATES PATENT AND TRADEMARK OFFICE
CERTIFICATE OF CORRECTION

PATENT NO.        : 7,520,859 B2
APPLICATION NO.   : 11/374263
DATED             : April 21, 2009
INVENTOR(S)       : Nunome Page 1 of 1

It is certified that error appears in the above-identified patent and that said Letters Patent is hereby corrected as shown below:

Col. 6, line 1: "addition of a" should read --addition of α--

Signed and Sealed this

Twenty-second Day of September, 2009

David J. Kappos
*Director of the United States Patent and Trademark Office*